United States Patent [19]
Heathman et al.

[11] Patent Number: 5,572,021
[45] Date of Patent: Nov. 5, 1996

[54] METHODS OF DETECTING THE LOCATIONS OF WELL TREATING FLUIDS

[75] Inventors: James F. Heathman, Duncan, Okla.; Robert F. Shelley, Kingsport, Tenn.; Jiten Chatterji, Duncan, Okla.

[73] Assignee: Halliburton Company, Duncan, Okla.

[21] Appl. No.: 432,501

[22] Filed: May 1, 1995

[51] Int. Cl.$^6$ .................................................. G01V 5/10
[52] U.S. Cl. .................. 250/269.5; 250/259; 250/302
[58] Field of Search ................................. 250/255, 259, 250/269.4, 269.5, 302, 256

[56] References Cited

U.S. PATENT DOCUMENTS

| | | | |
|---|---|---|---|
| 2,231,577 | 2/1941 | Hare | 250/259 X |
| 3,115,576 | 12/1963 | Rickard | 250/259 X |
| 5,083,029 | 1/1992 | Buchanan | 250/390.05 |
| 5,252,832 | 10/1993 | Nguyen et al. | 250/390.01 |

Primary Examiner—Constantine Hannaher
Assistant Examiner—Edward J. Glick
Attorney, Agent, or Firm—Craig W. Roddy; C. Clark Dougherty, Jr.

[57] ABSTRACT

Methods are provided for detecting the surface and/or subterranean locations of well treating fluids after the treating fluids have been introduced into wells and used for performing treatments therein. The methods of determining the subterranean locations of treating fluids basically comprise introducing a treating fluid into a well having a nonhazardous thermal neutron absorbing material combined therewith and performing a treatment in the well with the fluid. Fast neutrons from a source thereof are emitted in the well after the treatment whereby they interact with elements in the well and are thermalized. The thermal neutrons backscattered in the well are detected, and a count representing the detected thermal neutrons is generated. The subterranean locations of the treating fluid are determined by comparing the thermal neutron counts in the well before and after placement of the thermal neutron absorbing treating fluid therein.

27 Claims, No Drawings

METHODS OF DETECTING THE LOCATIONS OF WELL TREATING FLUIDS

BACKGROUND OF THE INVENTION

1. Field of the Invention

The present invention relates to methods of detecting the surface and/or subterranean locations of well treating fluids, and more particularly, to methods of detecting the location of such a fluid after the fluid has been introduced into a well and used for performing a treatment therein.

2. Description of the Prior Art

A variety of well treatments using treating fluids are performed in the completion and stimulation of oil and gas wells. For example, cementing treatments are carried out in the construction and repair of wells utilizing a cement composition as the treating fluid. In forming a cement composition, a hydraulic cement is normally mixed with water and other additives to form a pumpable cement composition which is placed in a subterranean zone penetrated by a well bore. After placement in the zone, the cement composition sets into a hard substantially impermeable mass in the zone.

High viscosity well treating fluids are also utilized in the construction of a well and in the stimulation of formations penetrated by the well bore to enhance the production of oil and gas therefrom. The most commonly used such treating fluids are high viscosity gelled fluids which are utilized in completion treatments such as in forming gravel packs and stimulation treatments such as hydraulic fracturing.

The most common cementing treatment or operation performed in the construction of a well is primary cementing whereby a metal pipe string such as casing or a liner is placed in the well bore and bonded therein by cement. Other cementing treatments utilized in wells are usually remedial in nature. For example, a cement composition is often squeezed into cracks or openings in pipe disposed in the well bore, in the cement sheath in the annulus between the pipe and the well bore, and in other similar locations and allowed to set therein whereby the cracks or openings are plugged.

An example of a stimulation procedure which is performed using a high viscosity treating fluid is hydraulic fracturing. Hydraulic fracturing is performed by injecting a high viscosity fluid through the well bore into a subterranean formation to be fractured and applying sufficient fluid pressure on the formation to cause its breakdown and the production of one or more fractures therein. A fracture proppant material such as sand or other particulate material is usually suspended in the high viscosity fracturing fluid whereby the proppant material is carried into the fractures and deposited therein. When pressure on the fractured formation is released, the fractures are propped open by the proppant material therein.

In all of the various completion and stimulation treatments where a treating fluid is introduced into a subterranean zone penetrated by a well bore, it is difficult to confirm that the treating fluid utilized has entered and/or filled the desired subterranean zone. As a result, methods of detecting the locations of a well treating fluid after it has been introduced into a well have heretofore been developed and used. Typically, a radioactive tracer material is included in the treating fluid and after the placement of the treating fluid containing the radioactive tracer, an instrument which detects radioactivity is lowered in the well and utilized to determine the location or locations of the treating fluid.

The monitoring of produced well fluids on the surface to ascertain the presence of a treatment fluid containing a tracer material previously injected into a well would be a valuable tool in determining the life and/or quality of the treatment. For example, wells are often chemically treated to prevent the formation of scale in the producing formation and related equipment. By detecting the concentration of the chemical in produced fluids, the duration of the treatment and the optimum time for repeating the treatment could be determined. However, if radioactive tracer material was used in such an application, the produced fluids containing the radioactive material would be contaminated and unsafe.

Radioactive tracers are expensive and are considered hazardous whereby they and the fluids containing them must be handled and disposed of in accordance with the laws and rules relating to hazardous materials. Thus, there is a need for an improved method of detecting the location of a well treating fluid after the treating fluid has been introduced into a well and used for performing a treatment therein which does not involve the use of radioactive tracer materials or other hazardous materials which must be disposed of in a special manner.

SUMMARY OF THE INVENTION

The present invention meets the above described needs by providing improved methods of detecting the presence and concentration of a treating fluid in surface produced well fluids and/or detecting the subterranean locations of the treating fluid after the treating fluid has been used for performing a well treatment. Instead of hazardous radioactive or other tracer materials which must be handled and disposed of in a special environmentally safe manner, the methods of the present invention utilize non-hazardous thermal neutron absorbing tracer materials and conventional thermal neutron detecting equipment.

The methods of the present invention for detecting the presence and concentration of a well treating fluid in surface fluids produced from a well after the treating fluid has been used to perform a treatment in the well basically comprise the following steps. A non-hazardous thermal neutron absorbing material is combined with the treating fluid, and the treating fluid containing the material is used to perform the treatment in the well. Thereafter, the surface fluids produced from the well are monitored for the presence and concentration of the treatment fluid therein by contacting the surface fluids with fast neutrons whereby the fast neutrons interact with elements in the surface fluids and are thermalized thereby. The thermal neutrons produced by the surface fluids are detected and a count representative of the detected thermal neutrons is generated. That count is then compared with a count representative of the detected thermal neutrons produced by the surface fluids when treating fluid and neutron absorbing material are not present therein to determine the differences in the counts and the presence and concentration of the treating fluid in the surface fluids. The differences in the counts are due to thermal neutrons being absorbed by the thermal neutron absorbing material in the treating fluid when the treating fluid is present in the surface fluids.

The methods of the present invention for detecting the subterranean locations of a well treating fluid after the treating fluid has been used for performing a treatment in a well basically comprise the following steps. A non-hazardous thermal neutron absorbing material is combined with the treating fluid, and the treating fluid containing the thermal neutron absorbing material is introduced into the well and used to perform the well treatment therein. Fast neutrons from a source thereof are emitted in the well whereby the fast neutrons interact with elements in the well and are thermalized thereby. Thermal neutrons which are backscattered in the well are detected, and a count representative of the detected thermal neutrons is generated over one or more selected subterranean intervals in the well. The subterranean locations of the treating fluid in the well are determined in response to the differences in the count generated after the performance of the well treatment and a count representative of the one or more subterranean intervals in the well before the well treatment. The differences in the before and after counts are due to thermal neutrons being absorbed by the thermal neutron absorbing material in the treating fluid.

Because the thermal neutron absorbing materials utilized in accordance with this invention are non-hazardous materials, produced surface fluids containing the materials and unused or recovered treating fluid containing the materials do not have to be handled or disposed of as hazardous fluids. Further, the thermal neutron absorbing materials utilized in accordance with this invention are relatively inexpensive as compared to radioactive tracer materials heretofore utilized.

It is, therefore, a general object of the present invention to provide improved methods of detecting the locations of well treating fluids.

A further object of the present invention is the provision of methods of detecting the presence and concentration of a treating fluid in surface produced well fluids and/or detecting the subterranean locations of a well treating fluid after the treating fluid has been used to perform a subterranean well treatment which do not utilize hazardous materials and are relatively inexpensive to carry out.

Other and further objects, features and advantages of the present invention will be readily apparent to those skilled in the art upon a reading of the description of preferred embodiments which follows.

DESCRIPTION OF PREFERRED EMBODIMENTS

The present invention provides improved methods of detecting the locations of a well treating fluid after the treating fluid has been introduced into a well and used for performing a treatment therein. The methods can be used to detect the presence of a treating fluid such as a scale inhibiting fluid in surface produced well fluids to thereby determine information such as when the treatment should be repeated. The methods can also be used to detect the subterranean locations of a well treating fluid after the treating fluid has been used for performing a subterranean treatment in the well.

In performing the methods of detecting the presence and concentration of a well treating fluid in surface fluids produced from a well after the treating fluid has been used for performing a treatment in the well, the following steps are carried out. A non-hazardous thermal neutron absorbing material of this invention is combined with the treating fluid to be used. The treating fluid including the thermal neutron absorbing material is introduced into the well and a well treatment is performed therewith. As mentioned above, an example of the treatment performed is the injection of scale inhibiting chemicals into the well and into the producing formation penetrated thereby. As formation fluids are produced from the well, portions of the treating fluid are also removed which lowers the concentration of the treating fluid in the formation. When the treating fluid in the formation falls to a minimum level as indicated by detecting the concentration of the treating fluid in surface well fluids, the treatment is repeated.

The presence and concentration of the well treating fluid in surface produced well fluids is detected in accordance with this invention by emitting fast neutrons from a source thereof into contact with the produced well fluids whereby the fast neutrons interact with elements in the fluid and are thermalized thereby. The thermal neutrons produced by the surface fluids are detected and a count representative of the detected thermal neutrons is generated. The presence and concentration of the treating fluid in the produced well fluids is determined by comparing the thermal neutron count generated with a count representative of the detected thermal neutrons produced by the surface well fluids when they do not contain the treating fluid and the thermal neutron absorbing material therein.

Conventional dual-spacing neutron tools (commonly referred to as DSN tools) are well known to those skilled in the art and have been utilized heretofore for running neutron logs of subterranean formations. Such tools commonly include a neutron source for emitting fast neutrons, a long spacing thermal neutron detector and a short spacing thermal neutron detector. Similar instruments which can be utilized to detect the presence and concentration of treating fluids containing a thermal neutron absorbing material in surface produced well fluids at the well site or at an off-site laboratory are also well known.

The methods of detecting the subterranean location of a well treating fluid after the treating fluid has been introduced into a well and used for performing a treatment therein are comprised of the following steps. A non-hazardous thermal neutron absorbing material of this invention is combined with the treating fluid to be utilized. The treating fluid including the thermal neutron absorbing material is then introduced into the well and a well treatment is performed therewith.

After the treatment, fast neutrons are emitted in the well. That is, a DSN neutron tool or the equivalent containing a source from which fast neutrons are emitted is lowered in the well bore whereby the fast neutrons interact with elements in the well and are thermalized thereby. The thermal neutrons produced are backscattered in the well and are detected by a thermal neutron detector in the tool. The detector generates a count representative of the detected thermal neutrons over one or more selected longitudinal subterranean intervals in the well, i.e., the intervals in the well where it is expected that treating fluid will be located after a treatment is performed in the well.

The subterranean locations of the treating fluid in the well are determined based on the differences in the count generated after the well treatment and a count representative of the one or more subterranean intervals in the well before the well treatment. That is, because the thermal neutron absorbing material in the treating fluid absorbs some of the thermal neutrons as they are generated in the well after the treatment, a comparison of the before and after counts correlated with the locations where the counts were generated indicates the subterranean locations of the treating fluid.

A thermal neutron count over the locations of interest in a well before the well treatment is performed may be available as a result of the performance of previous treatments therein, etc. If not, a before treatment count is determined prior to introducing the treating fluid into the well. That is, a tool containing a fast neutron source is lowered in the well bore whereby the fast neutrons interact with elements in the well and are thermalized. The thermal neutrons produced and backscattered in the well are detected by a thermal neutron detector as described above, and a count representative of the detected thermal neutrons over the one or more selected subterranean intervals in the well is produced.

The thermal neutron absorbing material which is utilized in accordance with the methods of this invention can be comprised of any element which has a thermal neutron absorbing capability of a magnitude such that differences in the backscattered thermal neutrons before and after a treating fluid containing the material is introduced into a well can be detected. However, certain elements which have a higher thermal neutron absorbing capacity than others are generally preferred. Particularly preferred such high capacity elements are cadmium and boron. Cadmium has a thermal neutron absorption cross-section of 2,520 barns while boron has a thermal neutron absorption cross-section of 767.4 barns.

Compounds comprised of cadmium or boron are preferred for use in accordance with this invention with boron compounds being the most preferred because boron has a significantly higher number of atoms per weight. Of the various cadmium and boron compounds which can be utilized, particularly suitable such compounds are cadmium hydroxide and carbon tetraboride (also known as boron carbide), with carbon tetraboride being the most preferred. Cadmium hydroxide and carbon tetraboride are both insoluble in aqueous treating fluids, do not pose any incompatibility problems, and are not hazardous to the environment. When used in treating fluids such as aqueous and non-aqueous hydraulic cement compositions, aqueous and non-aqueous high viscosity gelled liquids and aqueous and non-aqueous low viscosity liquids, cadmium hydroxide is generally added to the treating fluid in an amount in the range of from about 0.1% to about 5% by weight of the treating fluid.

From the standpoint of disposal, the use of insoluble thermal neutron absorbing materials is preferred. However, both insoluble and soluble neutron absorbing materials can be utilized in accordance with the methods of this invention. Soluble materials are best suited for some applications where solids settling and/or plugging of flow passages takes place, and the additional expense involved in disposing of treating fluids containing the soluble materials may be justifiable in those applications.

As mentioned above, the methods of the present invention are applicable to any subterranean well treatment which is performed using a treating fluid. The treating fluids can be any of the various fluids used for carrying out treatments in oil, gas and water wells. Generally, such fluids are water base fluids or hydrocarbon base fluids.

Treating fluids and treatments in which the methods of this invention are particularly applicable are cement compositions used for performing primary and other cementing operations such as remedial squeeze cementing. In such cementing procedures, an aqueous hydraulic cement composition is utilized generally comprised of hydraulic cement, water present in an amount sufficient to form a pumpable slurry and a variety of additives such as set retarding additives, fluid loss reducing additives and the like.

While various hydraulic cements can be utilized, Portland cement is generally preferred and can be, for example, one or more of the various types identified as API Classes A–H and J cements. These cements are described and defined in *API Specification For Materials And Testing For Well Cements,* API Specification 10A, 21st Edition, dated Sep. 1, 1991 of the American Petroleum Institute which is incorporated herein by reference. API Portland cements generally have a maximum particle size of about 90 microns and a specific surface (sometimes referred to as Blaine Fineness) of about 3,900 square centimeters per gram. A highly useful and effective cement slurry base for use in carrying out well cementing operations is comprised of API Portland cement mixed with water to provide a density of from about 11.3 to about 18.0 pounds per gallon.

It is often highly advantageous to use a fine particle size hydraulic cement, particularly in remedial operations involving squeeze cementing. Such fine particle size hydraulic cement generally consists of particles having diameters no larger than about 30 microns and having a Blaine Fineness no less than about 6,000 square centimeters per gram. Fine particle size hydraulic cements and their use in well completion and remedial operations are disclosed in U.S. Pat. No. 5,121,795 issued Jun. 16, 1992 to Ewert et al. and U.S. Pat. No. 5,125,455 issued Jun. 30, 1992 to Harris et al., both of which are incorporated herein by reference.

The water used in well cement compositions can be water from any source provided that it does not contain an excess of compounds which adversely react with or otherwise effect other components in the cement composition or interfere with the detection of the cement composition in accordance with this invention. Generally, the water is present in the range of from about 30% to about 60% by weight of dry cement in the composition when the cement is of normal particle size. When a cement of fine particle size as described above is used, water is generally present in the cement composition in an amount in the range of from about 100% to about 200% by weight of dry cement in the composition, and a dispersing agent such as the dispersing agent described in U.S. Pat. No. 4,557,763 issued on Dec. 10, 1985 to George et al. is generally included to facilitate the formation of the cement slurry and prevent the premature gelation thereof.

As is well understood by those skilled in the art, to obtain optimum results in well cementing applications, a variety of additives are included in the cement compositions utilized. Such additives are used in the cement compositions to vary the density, increase or decrease strength, accelerate or retard the time of setting, reduce fluid loss, etc. The preferred and most commonly utilized cement compositions for performing treatments in oil and gas wells are those meeting the specifications of the American Petroleum Institute comprising Portland cement mixed with water and other additives to provide a cement composition having properties appropriate for the conditions existing in each individual subterranean zone to be cemented.

A variety of hydrocarbon base and water base treating fluids are utilized for carrying out other well completion and stimulation treatments. For example, such fluids are utilized in completion treatments whereby gravel packs are formed in and adjacent to the well bore and in production stimulation treatments such as formation fracturing, acidizing, and fracture acidizing treatments. The most commonly used treating fluids for carrying out such completion and stimulation treatments are aqueous high viscosity gelled liquids. In formation fracturing treatments, proppant materials for propping the fractures open such as sand, glass beads, sintered bauxite, ceramic beads and the like are often included in the fracturing fluid.

In forming high viscosity gelled treating fluids, substantially any liquid including fresh water, salt water, brines, seawater, refined and unrefined hydrocarbons, and the like can be used so long as the liquid does not adversely react with other components making up the treating fluid or interfere with detection in accordance with this invention. However, the liquid most often employed is fresh water containing a low concentration of a clay stabilizing salt such as potassium chloride.

A gelling agent is added to the aqueous liquid to increase the viscosity thereof. While a variety of well known gelling agents can be used, polysaccharide gelling agents are the most commonly used for forming high viscosity gelled treating fluids. Such polysaccharide gelling agents are generally selected from the group consisting of galactomannan gums, modified or derivative galactomannan gums and cellulose derivatives. Examples of galactomannan gums which can be utilized include arabic gum, ghatti gum, karaya gum, tamarind gum, tragacanth gum, guar gum, locust bean gum and the like. Such gums can be modified such as by forming carboxyalkyl and hydroxyalkyl derivatives thereof. Examples of such derivatives which are particularly suitable are carboxymethyl guar and hydroxypropyl guar. Double derivatives can also be utilized, e.g., carboxymethylhydroxypropyl guar.

Modified celluloses and derivatives thereof can also be utilized as gelling agents. In general, any of the water soluble cellulose ethers can be used such as the various carboxyalkyl cellulose ethers, e.g., carboxyethyl cellulose and carboxymethyl cellulose. Mixed ethers such as carboxymethylhydroxyethyl cellulose and hydroxyalkyl celluloses such as hydroxyethyl cellulose can also be utilized. Further, alkyl celluloses such as methyl cellulose, and alkylhydroxyalkyl celluloses such as methylhydroxypropyl cellulose; alkylcarboxyalkyl celluloses such as ethylcarboxymethyl cellulose; alkylalkyl celluloses such as methylethyl cellulose; and hydroxyalkylalkyl celluloses such as hydroxypropylmethyl celluloses can all be utilized.

The preparation of high viscosity gelled aqueous treating fluids for carrying out treatments in subterranean formations or zones is well understood by those skilled in the art. The amount of gelling agent employed in the base aqueous liquid depends upon the desired final viscosity of the resulting solution. Generally, the gelling agent is combined with the aqueous liquid in an amount in the range of from about 10 pounds to about 200 pounds per 1,000 gallons of aqueous liquid. A polysaccharide gelled aqueous liquid which is not crosslinked (known in the art as a linear gel) can develop a relatively high viscosity, e.g., as high as from about 10 to about 300 centipoises measured on a Fann Model 35 viscometer at 70° F. and at an rpm of 3000. When a higher viscosity is required, such as when the gelled aqueous treating fluid is utilized as a fracturing fluid and must carry proppant material suspended therein, the gelled aqueous liquid can be crosslinked to further increase its viscosity. While a variety of crosslinking agents can be utilized for crosslinking a polysaccharide gelled aqueous liquid, particularly suitable such crosslinking agents are transition metal containing compounds which release transition metal ions when dissolved in an aqueous liquid. A borate releasing compound can also be utilized as a crosslinking agent as can other compounds known to those skilled in the art. The particular crosslinking agent utilized is generally combined with a gelled aqueous treating fluid in the form of an aqueous concentrate in an amount in the range of from about 0.1 gallon to about 5 gallons per 1,000 gallons of water in the treating fluid.

After a high viscosity gelled aqueous treating fluid has been introduced into a subterranean zone or formation and used to perform a completion or stimulation procedure therein, it is caused to revert to a relatively low viscosity liquid whereby it can be reverse flowed out of the well and recovered. Generally, the high viscosity treating fluid is converted into a low viscosity liquid after a desired period of time by including a gel breaker in the fluid prior to introducing it into the subterranean formation or zone. Heretofore utilized gel breakers include enzymes or water soluble persulfates and various other compounds well known to those skilled in the art. The quantity of gel breaker included in the aqueous high viscosity treating fluid is such that the treating fluid reverts to a thin recoverable fluid within from about 6 to about 24 hours after its introduction into a subterranean formation or zone.

Well treatments are also conducted using treating fluids comprised of low viscosity aqueous and non-aqueous liquids. Thus, the treating fluids utilized in accordance with this invention can be, in whole or in part, comprised of aqueous or non-aqueous hydraulic cement compositions, high viscosity gelled aqueous and non-aqueous treating fluids and low viscosity aqueous and non-aqueous treating fluids.

In all of the well completion and stimulating treatments using the treating fluids described above, it is often desirable to detect the subterranean location or locations of the treating fluid after the treating fluid has been introduced into the well and used for performing a treatment therein. For example, in performing a primary cementing treatment wherein casing or a liner is cemented in a well bore, a cement composition is pumped downwardly through the casing or liner and then upwardly into the annulus between the casing or liner and the walls of the well bore. Once the cement composition has been placed in the annulus, it is important to verify that the cement composition has uniformly filled the annulus over the entire length of casing or liner being cemented. In carrying out completion and stimulation treatments utilizing aqueous high viscosity gelled treating fluids, it is often desirable to verify that the treating fluid has entered a particular subterranean location.

Also, as mentioned above, in other well treatments using high or low viscosity treating fluids such as and similar to scale inhibiting treatments, it is often desirable to detect the presence and concentration of the treating fluid in the well fluids produced to the surface so that the proper timing of additional treatments can be determined, etc.

The present invention provides methods of detecting the presence and concentration of well treating fluids in the well fluids produced to the surface and of detecting the subterranean locations of well treating fluids by including a non-hazardous thermal neutron absorbing material in the treating fluid. As mentioned above, the thermal neutron absorbing material can be combined directly with the treating fluid. If desirable, however, the thermal neutron absorbing material can be combined with solid materials suspended in the treating fluid such as proppant materials. For example, the thermal neutron absorbing material can be adsorbed on the material or included therein when the proppant material is manufactured.

After a well treatment has been performed and the treating fluid utilized containing the thermal neutron absorbing material has been recovered, it as well as unused treating fluid can be easily and inexpensively disposed of using known techniques applicable to non-hazardous materials. Further, the methods of this invention utilize a source of fast neutrons to emit the neutrons in a well bore and one or more thermal neutron detectors to detect thermal neutrons produced by the interaction of the fast neutrons with elements in the well bore. Such sources, detectors and the interaction of fast neutrons with elements to form thermal neutrons are well known. The use of such sources and detectors in well applications is described in U.S. Pat. No. 5,083,029 issued Oct. 12, 1993 to Nguyen et al. and U.S. Pat. No. 5,083,029 issued Jan. 21, 1992 to Buchanan, both of which are assigned to the assignee of this present invention and are incorporated herein by reference.

The methods of the present invention are particularly suitable for use when performing primary cementing operations in a well utilizing cement compositions of the type described above. The methods of the invention for detecting the subterranean location of a cement composition after the cement composition has been used for the primary cementing of casing or a liner in a well bore are basically comprised of the following steps:

(a) prior to introducing the cement composition into the well, emitting fast neutrons from a source thereof within the casing or liner disposed in the well bore whereby the fast neutrons interact with elements in the well and are thermalized thereby;

(b) detecting thermal neutrons backscattered in the well and generating a count representative of the detected thermal neutrons over one or more selected subterranean longitudinal intervals in the well;

(c) combining a thermal neutron absorbing material with the cement composition to be used in performing the primary cementing operation, preferably a thermal neutron absorbing material selected from the group consisting of cadmium and boron compounds, more preferably cadmium hydroxide or carbon tetraboride, and most preferably carbon tetraboride;

(d) introducing the cement composition including the thermal neutron absorbing material into the well and into the annulus between the casing or liner and the well bore;

(e) again emitting fast neutrons from a source thereof within the casing or liner in the well bore whereby the fast neutrons interact with elements in the well and are thermalized thereby;

(f) again detecting thermal neutrons backscattered in the well and generating a count representative of the detected thermal neutrons over the one or more selected subterranean intervals in the well; and (g) determining the subterranean locations of the cement composition in the annulus between the casing or liner and the well bore in response to the differences in the counts generated in steps (b) and (f) due to thermal neutrons being absorbed by the thermal neutron absorbing material in the cement composition.

As will be understood, when a count representing the detected thermal neutrons in the well to be treated prior to performing a treatment therein is already known, steps (a) and (b) above can be omitted.

In order to further illustrate the methods of the present invention, the following example is given:

EXAMPLE

Test models of well bores were constructed approximately 10 feet long using 8⅝ inch OD casing as the outer jacket and 5.5 inch OD casing as the cemented casing. The cement slurry used as the treatment fluid consisted of a 16 pound per gallon Portland cement—fresh water mixture containing 2% by weight of dry cement of either cadmium hydroxide or carbon tetraboride.

The tests were run with fresh water in the casings of the test models and with three different formation materials around the outer jacket to obtain background effects of minerals of different types and porosities. One test was run in a water tank to have a background effect of water only.

A conventional dual-spacing neutron tool was utilized in the tests and the test results are expressed as the percent reduction in the count for the cement slurry containing cadmium hydroxide or carbon tetraboride as compared to the same cement slurry without cadmium hydroxide or carbon tetraboride, referred to as "Neat Cement". The results of these tests are given in the Table below.

| | | Count For Cement Slurry Tested, (% Of Count For Neat Cement) | | | |
| --- | --- | --- | --- | --- | --- |
| | Forma- | $Cd(OH)_2$ | | $CB_4$ | |
| | tion | | | | |
| Formation Mineral Used | Mineral Porosity (%) | Short Spacing Detector | Long Spacing Detector | Short Spacing Detector | Long Spacing Detector |
| Vermont Marble | 2 | 69 | 60 | 58 | 47 |
| Indiana Limestone | 12 | 65 | 59 | 61 | 57 |
| Austin Chalk | 25 | 66 | 65 | 58 | 56 |
| Water | — | 69 | 75 | 64 | 70 |

Thus, the present invention is well adapted to carry out the objects and advantages mentioned as well as those which are inherent therein. While numerous changes may be made by those skilled in the art, such changes are encompassed within the spirit of this invention as defined by the appended claims.

What is claimed is:

1. A method of detecting the presence and concentration of a well treating fluid in surface fluids produced from a well after the treating fluid has been used for performing a treatment in the well comprising the steps of:

(a) combining a non-hazardous thermal neutron absorbing material with said treating fluid;

(b) introducing said treating fluid including said thermal neutron absorbing material into said well and performing a well treatment in said well therewith;

(c) thereafter emitting fast neutrons from a source thereof into contact with surface fluids produced by said well whereby said fast neutrons interact with elements in said fluids and are thermalized thereby;

(d) detecting the thermal neutrons produced by said surface fluids and generating a count representative of the detected thermal neutrons; and (e) determining the presence and concentration of said treating fluid in said well fluids by comparing the count generated in step (d) with a count representative of the detected thermal neutrons produced by said surface fluids when they do not contain said treating fluid with said thermal neutron absorbing material therein.

2. The method of claim 1 wherein said thermal neutron absorbing material is combined with said treating fluid in accordance with step (a) in an amount such that sufficient thermal neutrons are absorbed thereby to make the determination of step (e).

3. The method of claim 1 wherein said treating fluid is selected from the group consisting of water base fluids and hydrocarbon base fluids.

4. The method of claim 1 wherein said thermal neutron absorbing material is selected from the group consisting of cadmium and boron compounds which do not adversely react with said treating fluid or adversely affect said well treatment performed therewith.

5. The method of claim 1 wherein said treating fluid is selected from the group consisting of aqueous and non-aqueous hydraulic cement compositions, high viscosity gelled aqueous and non-aqueous treating fluids and low viscosity aqueous and non-aqueous treating fluids.

6. The method of claim 1 wherein said thermal neutron absorbing material is selected from the group consisting of cadmium hydroxide and carbon tetraboride.

7. The method of claim 6 wherein said thermal neutron absorbing material is present in said treating fluid in an amount in the range of from about 0.1% to about 5% by weight of said treating fluid.

8. A method of detecting the subterranean location of a well treating fluid after the treating fluid has been introduced into a well and used for performing a treatment therein comprising the steps of:

(a) combining a nonhazardous thermal neutron absorbing material with said treating fluid, wherein said thermal neutron absorbing material is insoluble in water;

(b) introducing said treating fluid including said thermal neutron absorbing material into said well and performing a well treatment in said well therewith;

(c) emitting fast neutrons from a source thereof in said well whereby said fast neutrons interact with elements in said well and are thermalized thereby;

(d) detecting thermal neutrons backscattered in said well and generating a count representative of the detected thermal neutrons over one or more selected subterranean intervals in said well; and (e) determining the subterranean locations of said treating fluid in said well in response to the differences in said count generated in step (d) and a count representative of said one or more subterranean intervals in said well before the well treatment of step (b) is performed due to thermal neutrons being absorbed by said thermal neutron absorbing material in said treating fluid.

9. The method of claim 8 which further comprises the steps of:

prior to introducing said treating fluid into said well in accordance with step (b), emitting fast neutrons from a source thereof in said well whereby said fast neutrons interact with elements in said well and are thermalized thereby; and detecting thermal neutrons backscattered in said well and generating the count utilized in step (e) which is representative of said one or more intervals in said well without said treating fluid therein.

10. The method of claim 8 wherein said thermal neutron absorbing material is combined with said treating fluid in accordance with step (a) in an amount such that sufficient thermal neutrons are absorbed thereby to make the determination of step (e).

11. The method of claim 8 wherein said treating fluid is selected from the group consisting of water base fluids and hydrocarbon base fluids.

12. The method of claim 8 wherein said thermal neutron absorbing material is selected from the group consisting of cadmium and boron compounds which do not adversely react with said treating fluid or adversely affect said well treatment performed therewith.

13. The method of claim 8 wherein said treating fluid is selected from the group consisting of aqueous and non-aqueous hydraulic cement compositions, high viscosity gelled aqueous and non-aqueous treating fluids and low viscosity aqueous and non-aqueous treating fluids.

14. The method of claim 8 wherein said thermal neutron absorbing material is selected from the group consisting of cadmium hydroxide and carbon tetraboride.

15. The method of claim 8 wherein said treating fluid is an aqueous hydraulic cement composition, said treatment performed in said well is primary cementing and said thermal neutron absorbing material is selected from the group consisting of cadmium hydroxide and carbon tetraboride.

16. The method of claim 15 wherein said thermal neutron absorbing material is present in said cement composition in an amount in the range of from about 0.1% to about 5% by weight of said composition.

17. A method of detecting the subterranean location of an aqueous hydraulic cement composition after the cement composition has been introduced into a zone to be cemented in a well comprising the steps of:

(a) combining a nonhazardous thermal neutron absorbing material with said cement composition, wherein said thermal neutron absorbing material is insoluble in water;

(b) introducing said cement composition including said thermal neutron absorbing material into said zone to be cemented;

(c) emitting fast neutrons from a source thereof in said well whereby said fast neutrons interact with elements in said well and are thermalized thereby;

(d) detecting thermal neutrons backscattered in said well and generating a count representative of the detected thermal neutrons over one or more selected subterranean intervals in said well; and (e) determining the subterranean locations of said cement composition in said well in response to the differences in said counts generated in step (d) and a count representative of said one or more subterranean intervals in said well before said cement composition is introduced therein in accordance with step (b) due to thermal neutrons being absorbed by said thermal neutron absorbing material in said cement composition.

18. The method of claim 17 which further comprises the steps of:

prior to introducing said treating fluid into said well in accordance with step (b), emitting fast neutrons from a source thereof in said well whereby said fast neutrons interact with elements in said well and are thermalized thereby; and detecting thermal neutrons backscattered in said well and generating the count utilized in step (e) which is representative of said one or more intervals in said well without said treating fluid therein.

19. The method of claim 17 wherein said thermal neutron absorbing material is combined with said cement composition in accordance with step (a) in an amount such that sufficient thermal neutrons are absorbed thereby to make the determination of step (e).

20. The method of claim 19 wherein said thermal neutron absorbing material is selected from the group consisting of cadmium and boron compounds which do not adversely react with said cement composition.

21. The method of claim 20 wherein said thermal neutron absorbing material is selected from the group consisting of cadmium hydroxide and carbon tetraboride.

22. The method of claim 21 wherein said thermal neutron absorbing material is present in said cement composition in an amount in the range of from about 0.1% to about 5% by weight of said composition.

23. A method of detecting the subterranean location of a well treating fluid after the treating fluid has been introduced into a well and used for performing a treatment therein comprising the steps of:

(a) prior to introducing said treating fluid into said well, emitting fast neutrons from a source thereof in said well whereby said fast neutrons interact with elements in said well and are thermalized thereby;

(b) detecting thermal neutrons backscattered in said well and generating a count representative of the detected thermal neutrons over one or more selected subterranean intervals in said well;

(c) combining a nonhazardous thermal neutron absorbing material with said treating fluid, wherein said thermal neutron absorbing material is insoluble in water;

(d) introducing said treating fluid including said thermal neutron absorbing material into said well and performing a well treatment in said well therewith;

(e) again emitting fast neutrons from a source thereof in said well whereby said fast neutrons interact with elements in said well and are thermalized thereby;

(f) again detecting thermal neutrons backscattered in said well and generating a count representative of the detected thermal neutrons over said one or more selected subterranean intervals in said well; and (g) determining the subterranean locations of said treating fluid in said well in response to the differences in said counts generated in steps (b) and (f) due to thermal neutrons being absorbed by said thermal neutron absorbing material in said treating fluid.

24. The method of claim 23 wherein said thermal neutron absorbing material is combined with said treating fluid in accordance with step (a) in an amount such that sufficient thermal neutrons are absorbed thereby to make the determination of step (g).

25. The method of claim 24 wherein said thermal neutron absorbing material is selected from the group consisting of cadmium and boron compounds.

26. The method of claim 25 wherein said thermal neutron absorbing material is selected from the group consisting of cadmium hydroxide and carbon tetraboride.

27. The method of claim 26 wherein said thermal neutron absorbing material is present in said treating fluid in an amount in the range of from about 0.1% to about 5% by weight of said treating fluid.

* * * * *